United States Patent
Clementi et al.

(10) Patent No.: US 8,802,726 B2
(45) Date of Patent: *Aug. 12, 2014

(54) USE OF NITROOXYDERIVATIVE OF DRUG FOR THE TREATMENT OF MUSCULAR DYSTROPHIES

(71) Applicant: Nicox S.A., Sophia Antipolis-Valbonne (FR)

(72) Inventors: Emilio Clementi, Milan (IT); Giulio Cossu, Milan (IT); Silvia Brunelli, Milan (IT); Ennio Ongini, Segrate (IT); Daniela Miglietta, Monza (IT)

(73) Assignee: Nicox S.A., Sophia Antipolis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/669,296

(22) Filed: Nov. 5, 2012

(65) Prior Publication Data

US 2013/0137765 A1  May 30, 2013

Related U.S. Application Data

(63) Continuation-in-part of application No. 12/159,577, filed as application No. PCT/EP2007/050630 on Jan. 23, 2007, now Pat. No. 8,575,222.

(60) Provisional application No. 60/764,755, filed on Feb. 3, 2006.

(51) Int. Cl.
*A01N 37/00* (2006.01)
*A61K 31/21* (2006.01)
*C07C 201/00* (2006.01)
*C07C 205/00* (2006.01)

(52) U.S. Cl.
USPC .......................................... 514/509; 568/924

(58) Field of Classification Search
CPC ...... A61K 31/04; C07C 15/24; C07C 203/02; C07C 203/04
USPC .................................... 514/740, 509; 568/924
See application file for complete search history.

(56) References Cited

U.S. PATENT DOCUMENTS

| | | |
|---|---|---|
| 6,610,676 B1 | 8/2003 | Del Soldato |
| 6,909,007 B1 | 6/2005 | Del Soldato |
| 2006/0052594 A1 | 3/2006 | Del Soldato et al. |

FOREIGN PATENT DOCUMENTS

| | | |
|---|---|---|
| EP | 1 336 602 A1 | 8/2003 |
| WO | WO 9509831 A1 * | 4/1995 |
| WO | WO 98/15568 A2 | 4/1998 |
| WO | WO 00/61604 A2 | 10/2000 |
| WO | WO 03/064443 A2 | 8/2003 |
| WO | WO 2006130982 A1 * | 12/2006 |
| WO | WO 2007/025632 A2 | 3/2007 |

OTHER PUBLICATIONS

Baraldi, Pier Giovanni et al., "Synthesis of Nitro Esters of Prednisolone, New Compounds Combining Pharmacological Properties of Both Glucocorticoids and Nitric Oxide"; Journal of Medicinal Chemistry; 47(3); 711-719 Coden: JMCMAR; ISSN: 0022-2623; 2004; p. 712; XP002475140; figure 1.

Perretti, M. et al.; "Generation of innovative anti-inflammatory and anti-arthritic glucocorticoid derivatives that release NO: the nitro-steroids"; Digestive and Liver Disease, 35 (Suppl. 2); S41-S48 Coden: DLDIFK; ISSN: 1590-8658; 2003; XP002475141; p. S43; figure 2.

* cited by examiner

*Primary Examiner* — Sarah Pihonak
(74) *Attorney, Agent, or Firm* — Arent Fox LLP

(57) ABSTRACT

The present invention relates to the use of nitric oxide releasing compounds for retarding or reversing muscular dystrophies such as Duchenne and Becker dystrophies.

4 Claims, No Drawings

USE OF NITROOXYDERIVATIVE OF DRUG FOR THE TREATMENT OF MUSCULAR DYSTROPHIES

CROSS REFERENCE TO RELATED APPLICATION

This application is a continuation-in-part of U.S. patent application Ser. No. 12/159,577, filed Jun. 27, 2008, which is a National Stage of International Application PCT/EP2007/050630, filed Jan. 23, 2007.

The present invention relates to the use of nitric oxide releasing compounds for retarding or reversing muscular dystrophies such as Duchenne and Becker dystrophies.

Muscular dystrophies are caused by progressive degeneration of skeletal muscle fibres. Lack of one of several proteins located either at the plasma membrane or within internal membranes, increases the probability of damage during contraction, and eventually leads to fibre degeneration, accompanied by severe local inflammation with infiltration of immune-competent cells.

Muscular dystrophies encompasse a group of inherited, progressive muscle disorders, distinguished clinically by the selective distribution of skeletal muscle weakness. The two most common forms of muscle dystrophy are Duchenne and Becker dystrophies, each resulting from the inheritance of a mutation in the dystrophin gene, which is located at the Xp21 locus. Other dystrophies include, but are not limited to, limb-girdle muscular dystrophy, fascioscapulohumeral (Landouzy-Dejerine) muscular dystrophy, congenital muscular dystrophy, myotonic dystrophy, and Emery-Dreifuss muscular dystrophy.

In the most severe form, such as Duchenne muscular dystrophy, regeneration is exhausted and skeletal muscle is progressively replaced by fat and fibrous tissue. This condition leads to patient showing a progressive weakness and eventually death by respiratory and/or cardiac failure.

The symptoms of Duchenne muscular dystrophy occur almost exclusively in males, and start at about 3-7 years of age with most patients confined to a wheelchair by 10-12 years and many die at about 20 years of age due to respiratory complications.

Of the different medications that have been tried as potential treatments for Duchenne muscular dystrophy, only the corticosteroids such as prednisone, prednisolone and deflazacort have shown potential for providing temporary improvement. This improvement results mainly from slowing the rate of progression or stabilizing muscle strength and function. Corticosteroid therapy also leads to side effects; as yet there is no consensus regarding their use as standard treatment.

Corticosteroids, such as prednisone, are believed to act by blocking the immune cell activation and infiltration which are precipitated by muscle fiber damage resulting from the disease.

The long-term therapies with corticosteroids as the remedy for muscular dystrophy, are associated with adverse effects such as osteoporosis, hypertension and Cushing syndrome, weight gain, cataracts, short stature, gastrointestinal symptoms, behavioural changes in case of the prednisolone and weight gain and cataracts as for deflazacort.

Bredt D. S. in Proc. Natl. Acad. Sci. USA 95 (1998), 14592-14593 reports that nitric oxide (NO) generated by muscular NO synthase, which is structurally and functionally linked to the dystrophin complex at the sarcolemma, participates to physiological development and function of skeletal muscle by regulating vasodilation and thus supply oxygen during exercise, by increasing glucose uptake in the myofibres and by regulating the enzymes activity relevant to cell energy metabolism.

EP 759899 describes nitrooxy derivative of NSAIDs. The pharmacological data reported in the document show that these compounds show a good anti-inflammatory, analgesic and antithrombotic activities and an increased gastric tolerability than the correspondent parent drug. The document does not report that these compounds are active for the treatment of muscular degenerative diseases.

WO 2004/105754 describes statins nitroderivatives, which exhibit strong anti-inflammatory, antithrombotic and antiplatelet activities. The document reports that the statins nitroderivatives can be used for treating or preventing cardiovascular diseases and peripheral vascular diseases and all disorders associated with endothelial dysfunctions such as vascular complications in diabetic patients and atherosclerosis. Also this document does not report that these compounds are active for the treatment of muscular degenerative diseases.

WO 00/53191 discloses the use of nitric oxide (NO), NO donors, inhibitor of NO activity or regulator of NO production for the treatment of muscle diseases which include Duchenne dystrophy, Becker dystrophy, limb-girdle muscular dystrophy, fascioscapulohumeral (Landouzy-Dejerine) muscular dystrophy, congenital muscular dystrophy, myotonic dystrophy, and Emery-Dreifuss muscular dystrophy.

In particular the document discloses the results of a study of mdx dystrophic mice treated with deflazacort, deflazacort plus L-NAME (a NOS enzymes inhibitor) or deflazacort plus L-arginine (a NO donor). In the experiment muscle tissues of tibialis anterior muscle and diaphragm were collected from the treated animal and the central nucleation index (CNI), which is a useful measure of muscle damage index, was assessed. The results show that the addition of the NO donor to deflazacort did not improve the status of muscles in mdx mice and that L-NAME augmented the beneficial effects of deflazacort only on diaphragm. The author concluded that the results show that L-NAME o other NOS inhibitors can be used for improve the effects of steroid when applied in situ.

Thus, there is a need to identify therapeutic agents which slow the muscle fibres damage and delay the onset of disability in patients with muscular dystrophies, but cause a lesser degree of skeletal muscle atrophy than current therapies.

Quite surprisingly and unexpectedly, it was found that nitric oxide releasing compounds of formula M-X—Y—$ONO_2$ wherein M is the residue of a therapeutic agent which is an NSAID or a statin are effective for retarding or reversing (treatment) muscular dystrophies. Moreover they have the advantage that they induce fewer adverse side effects, they are well tolerated by the patients and therefore they can be used in long term therapies.

It is an object of the present invention the use of nitric oxide releasing drugs of formula (Ia)

$$M\text{-}X\text{—}Y\text{—}ONO_2 \qquad (Ia)$$

or enantiomers or diasteroisomers thereof for the treatment of muscular dystrophies, wherein in the general formula (Ia) M, X and Y have the following meanings:

M is the residue selected from:
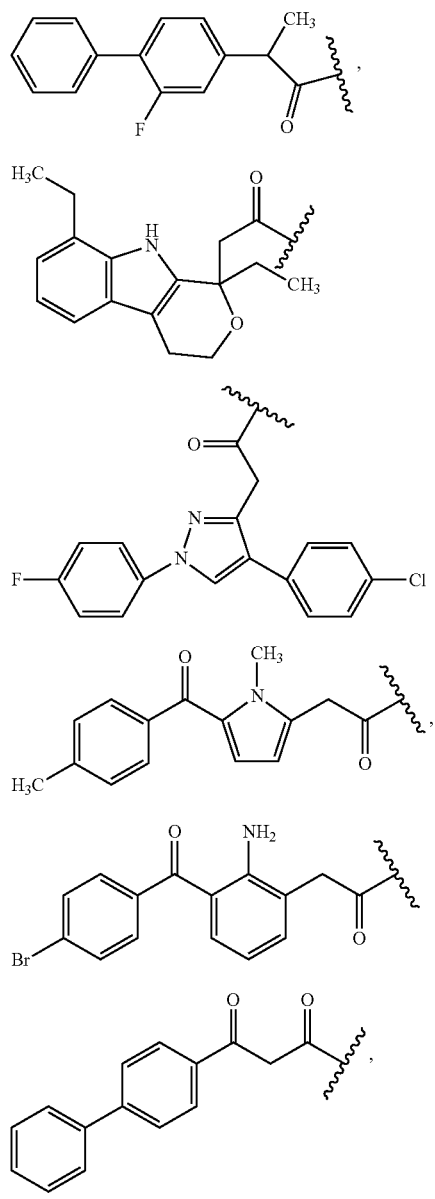
wherein $R_A$ is an hydrogen atom or —C(O)CH$_3$,
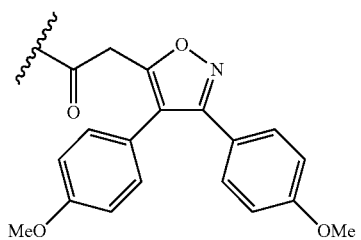
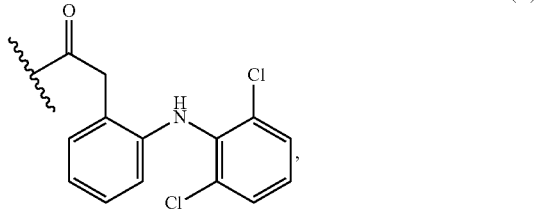
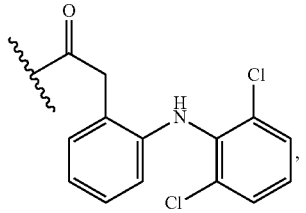
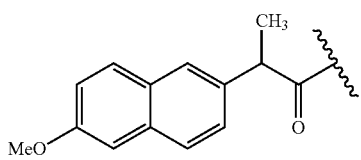
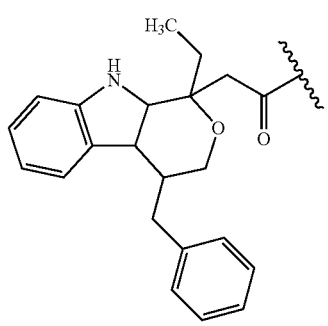
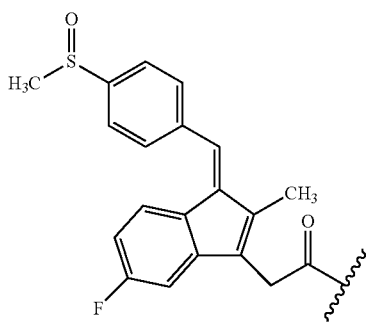
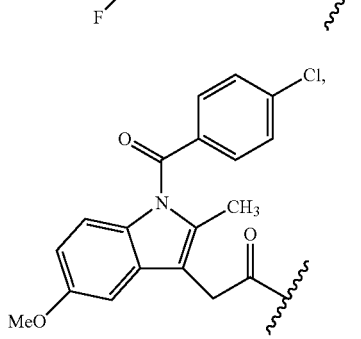

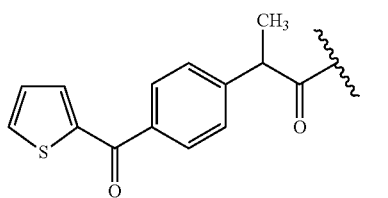 (XV)
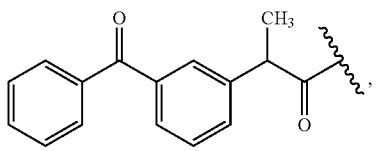 (XVI)
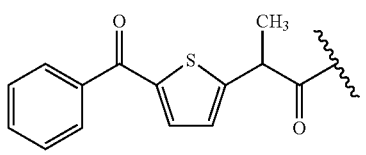 (XVII)
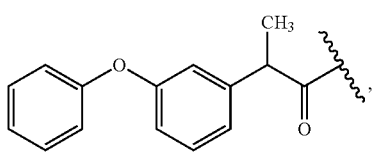 (XVIII)
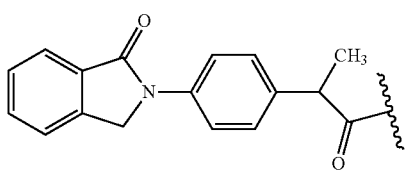 (XIX)
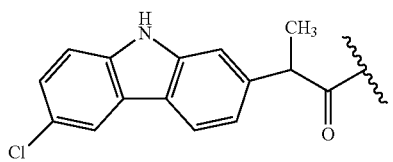 (XX)
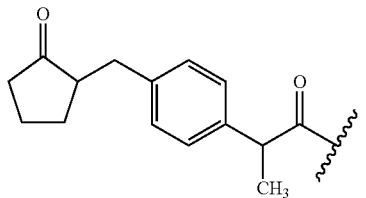 (XXI)
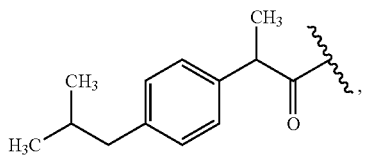 (XXII)
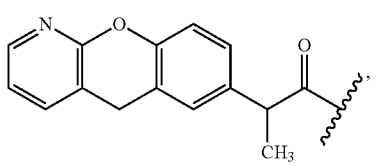 (XXIII)
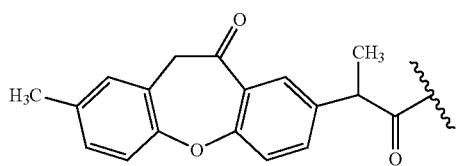 (XXIV)
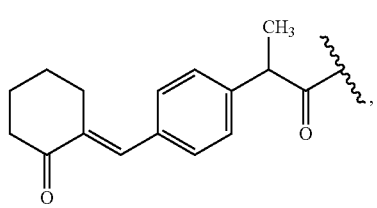 (XXV)
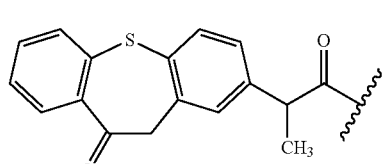 (XXVI)
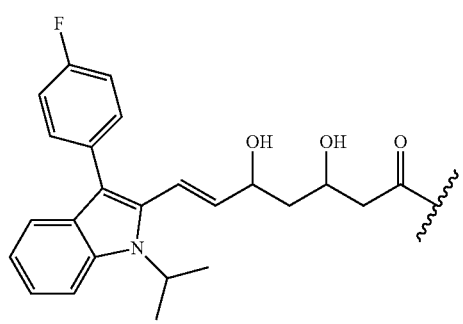 (XXXIV)
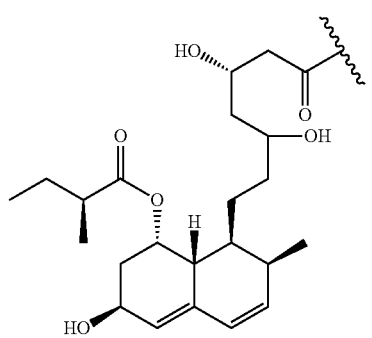 (XXXV)
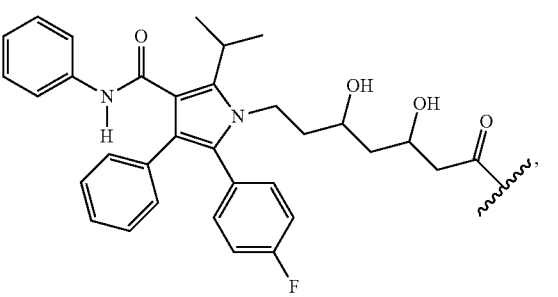 (XXXVI)

(XXXVII)

[Chemical structure with 4-fluorophenyl, pyridine with isopropyl groups, MeOCH2, and OH-OH-ketone chain]

(XXXIX)

[Chemical structure with 4-fluorophenyl, pyrimidine with methylsulfonyl-N-methyl amino and isopropyl, OH-OH-ketone chain]

X is —O—, —S— or —NR$^1$—, wherein R$^1$ is H or linear or branched $C_1$-$C_6$ alkyl;

Y is a bivalent radical having the following meanings:

a) straight or branched $C_1$-$C_{20}$ alkylene, preferably $C_1$-$C_{10}$, being optionally substituted with one or more of the substituents selected from the group consisting of: halogen atoms, hydroxy, —ONO$_2$ or T, wherein T is —OC(O)($C_1$-$C_{10}$ alkyl)-ONO$_2$ or —O($C_1$-$C_{10}$ alkyl)-ONO$_2$; more preferably Y is $C_1$-$C_{20}$ alkylene;

$C_5$-$C_7$ cycloalkylene group optionally substituted with linear or branched $C_1$-$C_{10}$ alkyl group, preferably CH$_3$;

b) (XXVII)

[Structure: —(CH$_2$)$_n$—phenyl—(CH$_2$)$_{n^1}$—]

c) (XXVIII)

[Structure: —(CH$_2$)$_n$—pyridyl(COOH)—(CH$_2$)$_{n^1}$—]

wherein n is an integer from 0 to 20, preferably n is an integer from 0 to 5, more preferably n is 0;

n$^1$ is an integer from 1 to 20, preferably n$^1$ is an integer from 1 to 5, more preferably n$^1$ is 1;

with the proviso that when Y is selected from the bivalent radicals mentioned under b) and c) then the —ONO$_2$ group of formula (I) is bound to —(CH$_2$)$_{n^1}$—;

d) (XXIX)

[Structure: —phenyl(OR$^2$)$_{n2}$—X$_1$—(CH$_2$)$_{na}$—]

wherein
X$_1$=—OCO— or —COO— and R$^2$ is H or CH$_3$;
na is an integer from 1 to 20; preferably n is an integer from 1 to 5;
n$_2$ is an integer from 0 to 2;

e) (XXX)

[Structure: —phenyl(OR$^2$)$_{n2}$—Y$^1$—X$_1$—(CH$_2$)$_{na}$—]

wherein:
Y$^1$ is —CH$_2$—CH$_2$—(CH$_2$)$_{n^2}$—; or —CH═CH—(CH$_2$)$_{n^2}$—;
X$_1$, na, n$^2$ and R$^2$ are as defined above;

f) (XXXI)

[Structure: R$^2$R$^2$C(NHR$^3$)—C(O)—O—(CH$_2$)$_{na}$—]

wherein:
na and R$^2$ are as defined above, R$^3$ is H or —COCH$_3$;
with the proviso that when Y is selected from the bivalent radicals mentioned under d)-f) then the —ONO$_2$ group of formula (I) is bound to —(CH$_2$)$_{na}$;
with the proviso that when X is —NR$^1$—, wherein R$^1$ is as above defined Y cannot be f);

g)

(XXXII)

—(CH—CH$_2$—X$_2$)$_{n^3}$—CH—CH$_2$—
   |                              |
   R$^2$                          R$^2$ (XXXIII)

R$^2$                   R$^2$
        |                        |
—(CH$_2$—CH—X$_2$)$_{n^3}$—CH$_2$—CH— wherein
X$_2$ is —O— or —S—;
n$^3$ is an integer from 1 to 6, preferably from 1 to 4, and R$^2$ is as defined above.

One preferred embodiment of the invention comprises the use of the nitric oxide releasing drug of formula (Ib)

(Ib)

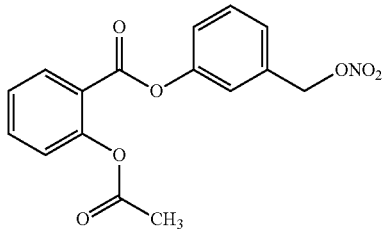

for the treatment of muscular dystrophies; the compound of formula (Ib) is known as 2-(acetyloxy)benzoic acid 3-(nitrooxymethyl)phenyl ester of formula.

Another preferred embodiment of the invention comprises the use of the nitric oxide releasing drug of formula (IIIb) or its enantiomers (IIIb)

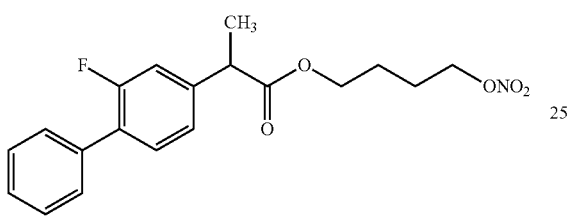

for the retarding or reversing muscular dystrophies; the compound of formula (IIIb) is known as 2-fluoro-alfa-methyl-4 [1,1'-biphenyl]4-acetic acid 4-nitrooxybutyl ester.

Another preferred embodiment of the invention comprises the use of a nitric oxide-releasing drug of formula (Ia) for treatment of muscular dystrophies, wherein in formula (Ia) M is selected from the group consisting of:

(XXXIV)

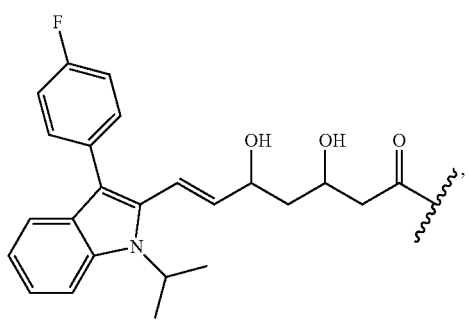

(XXXV)

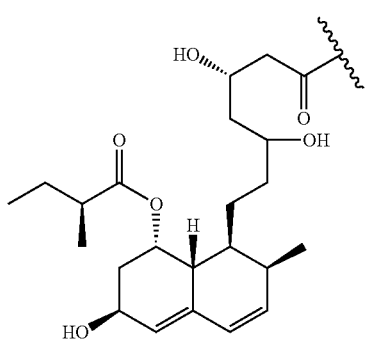

(XXXVI)

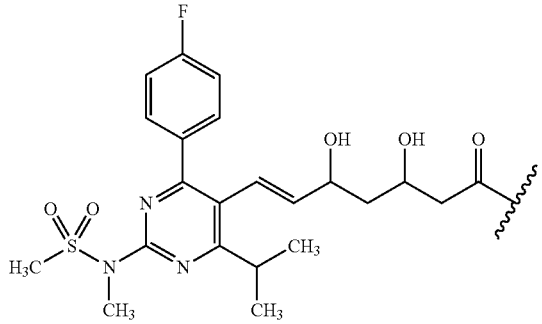

(XXXVII)

(XXXIX)

X is an oxygen atom,
Y is selected from:
  straight $C_1$-$C_{10}$ alkylene;
b)

(XXVII)

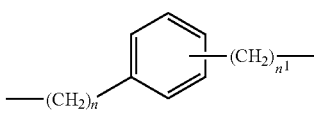

wherein n is an integer from 0 to 5; and
$n^1$ is an integer from 1 to 5, more preferably $n^1$ is 1;

Another preferred embodiment is the use for the treatment of muscular dystrophies of a nitric oxide-releasing drug selected from the group consisting of:

(XXXVb)

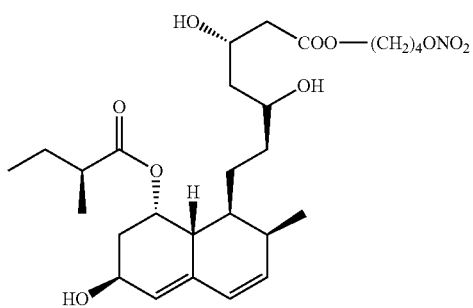

which is known as [1S-[1α(βS*,δS*),2α,6α,8β-(R*),8aα]]-1,2,6,7,8,8a-hexahydro-β,δ,6-trihydroxy-2-methyl-8-(2-methyl-1-oxobutoxy)-1-naphthaleneheptanoic acid 4-(nitrooxy)butyl ester or as pravastatin 4-(nitrooxy)butyl ester;

(XXXVc)

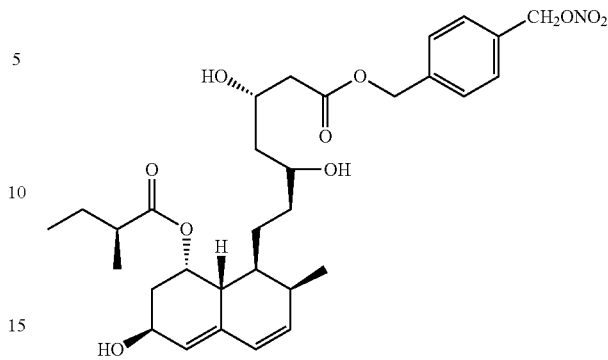

which is known as [1S-[1α(βS*,δS*),2α,6α,8β-(R*),8aα]]-1,2,6,7,8,8a-hexahydro-β,δ,6-trihydroxy-2-methyl-8-(2-methyl-1-oxobutoxy)-1-naphthaleneheptanoic acid 4 (nitrooxymethyl)benzyl ester or as pravastatin 4-(nitrooxymethyl)benzyl ester (XXXVIIb)

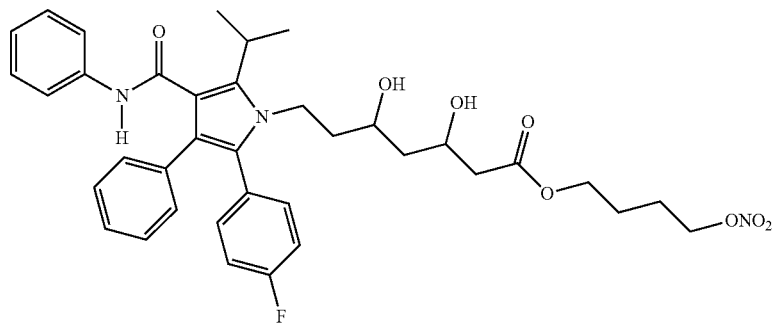

which is known as (βR,δR)-2(4-fluorophenyl)-β,δ-dihydroxy-5-(1-methylethyl)-3-phenyl-4-[(phenylamino)carbon-yl]-1H-pyrrole-1-heptanoic acid 3-(nitrooxy)butyl ester or as atorvastatin 3-(nitrooxy)butyl ester;

(XXXVIIc)

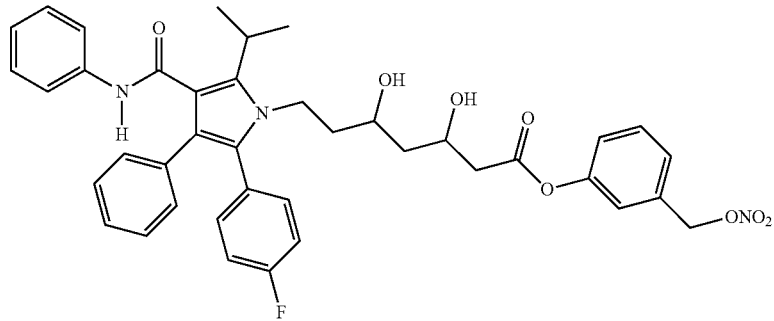

which is known as (βR,δR)-2(4-fluorophenyl)-β,δ-dihydroxy-5-(1-methylethyl)-3-phenyl-4-[(phenylamino)carbon-yl]-1H-pyrrole-1-heptanoic acid 3-(nitrooxymethyl)benzyl ester or as atorvastatin 3-(nitrooxymethyl)benzyl ester.

The doses to be administered are determined depending upon, for example, age, body weight, symptom, the desired therapeutic effect, the route of administration, and the duration of the treatment. In the human adult, the doses per person at a time are generally from 1 mg to 1000 mg, by oral administration, up to several times per day, and from 1 mg to 100 mg, by parenteral administration (preferably intravenous administration), up to several times per day, or continuous administration for from 1 to 24 hours.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

The general synthesis of the nitric oxide-releasing drug of formula (Ia) wherein M is selected from the residues of formulae (I)-(XXIV) and X are as above defined, is described in the EP 7 559 899

The process of synthesis of 2-(acetyloxy)benzoic acid 3-(nitrooxymethyl)phenyl ester of formula (Ib) is described in EP 1 194 397.

The general synthesis of nitric oxide-releasing of formula (Ia) wherein M is selected from the residues of formulae (XXXIV)-(XXXIX) and the synthesis of pravastatin 4-(nitrooxy)butyl ester are described in WO 2004/105754.

EXAMPLE 1

Muscular Dystrophy Model
(α-Sarcoglycan-Deficient Mice)

Reference for animal model: Duclos F. et al. J. Cell Biol. 1998 Sep. 21; 142(6):1461-71.
The tested compounds area
    2-acetyloxy benzoic acid 3-(nitrooxymethyl)benzoate of formula (Ib);
    pravastatin 4-(nitrooxy)butyl ester which of formula (XXXVb);
    2-fluoro-alfa-methyl-4[1,1'-biphenyl]4-acetic acid 4-nitrooxybutyl ester of formula (IIIb);
    prednisolone as reference corticosteroid drug.
Four groups of α-sarcoglycan (SG)-null C57BL/6 mice were treated with 2-acetyloxy benzoic acid 3-(nitrooxymethyl)benzoate (compound Ib) (100 mg/kg), pravastatin 4-(nitrooxy)butyl ester (compound XXXVb)(12 mg/kg), 2-fluoro-alfa-methyl-4[1,1'-biphenyl]4-acetic acid 4-nitrooxybutyl ester (compound IIIb)(30 mg/kg), prednisolone (3 mg/kg) or vehicle, administered daily in the diet.
At indicated time-points (ranging from 20 to 80 days) skeletal muscle function was tested by the free wheel test. 24 hours later animals were sacrificed, tissue isolated and histological characteristics analysed. Infiltrates were assessed after staining with the Azan Mallory technique; Necrotic fibres were measured in hematoxilin-stained sections; creatin kinase was measured using a commercially available kit on blood samples obtained 24 hours prior to the wheel test. (Sampaolesi M., et al Science 301, 487-492, 2003). The data are reported in table 1.

Free Wheel Running:
Voluntary wheel running was used as the exercise paradigm to avoid any physiological changes that may occur due to the stress of forced treadmill running. Mice were housed singly for a 24 hour period in a polycarbonate running wheel equipped with a magnetic counter, the output of which was sent to a speedometer, allowing quantification of the number of revolutions per day. The data are reported in table 2.

Creatine Kinase Activity Measurements:
quantitative and kinetic determination of creatine kinase activity in serum of control and drug treated-animals was measured using creatine kinase reagent (Sigma), according to the manufacturer's instructions. Blood was collected from tail of 2-7 months-old mice and serum obtained after centrifugation at 13.000 rpm for 10 minutes was stored at −80° C. before measurements. The data are reported in table 1.

Histology:
Diaphragm and tibialis anterior of untreated and drug-treated mice were isolated and included in Killik frozen section medium, quickly frozen and cut into 8-μm thick sections with the muscle fibres oriented transversely using a cryostat. Sections were stained with either Hematoxylin & Eosin or Azan Mallory, to evaluate the number of inflammatory infiltrates and necrotic fibres (18-10 sections for tissue). The data are reported in table 1.

The results show that the tested compounds (Ib), (XXXVb) and (IIIb) were significantly effective in reducing the histological, functional and biochemical alterations which typically occur in these animals. In particular, treated animals showed significantly reduced inflammatory infiltrates and almost undetectable necrotic fibres. (Table 1)

Plasma levels of creatin kinase, a hallmark of muscle damage, were significantly lower in treated animals; consistently, they performed significantly better on the free-wheel running test. (table 2)

Altogether the data show that the compounds of the present invention have a better profile as compared to prednisolone that is the drug of choice for this pathology.

TABLE 1

| Compound | Days of treat. | Histology data | |
|---|---|---|---|
| | | N° of inflammatory Infiltrates/section | N° of necrotic Fibres/section |
| Control (n = 3) | 80 | 192.6 ± 46.5 | 263.2 ± 43 |
| (XXXVb) (n = 5) | 80 | 54.2 ± 8.05** | 35 ± 2.1** |
| (Ib) (n = 5) | 80 | 91.3 ± 34.5* | 124.1 ± 33** |
| (IIIb) (n = 5) | 80 | 84.2 ± 22.5** | 48.4 ± 2.3** |
| Prednisolone | 80 | 59.4 ± 7.00** | 197.1 ± 23** |

**$P < 0.01$;
*$P < 0.05$ vs. control

TABLE 2

| Compound | Days of treatment | CK plasma level (U/ml) | Free wheel test (km/24 h) |
|---|---|---|---|
| Control (n = 3) | 20 | 595.2 ± 87 | 0.34 ± 0.02 |
| | 40 | 892.0 ± 96 | 0.06 ± 0.03 |
| | 60 | 844.3 ± 50 | 0.11 ± 0.02 |
| | 80 | 979.8 ± 91 | 0.14 ± 0.05 |

TABLE 2-continued

| Compound | Days of treatment | CK plasma level (U/ml) | Free wheel test (km/24 h) |
|---|---|---|---|
| (XXXVb) | 20 | 440.6 ± 33** | 0.55 ± 0.03** |
| (n = 5) | 40 | 488.2 ± 96.5* | 0.58 ± 0.01** |
|  | 60 | 627.4 ± 69.3** | 0.54 ± 0.03** |
|  | 80 | 614.8 ± 37** | 0.65 ± 0.05** |
| (Ib) | 20 | 665.6 ± 51 | 0.65 ± 0.07** |
| (n = 5) | 40 | 944.0 ± 95.5 | 0.42 ± 0.08** |
|  | 60 | 444.2 ± 20.2** | 0.31 ± 0.1* |
|  | 80 | 494.6 ± 56.1** |  |
| (IIIb) | 20 | 662.6 ± 41 | 0.95 ± 0.1** |
| (n = 5) | 40 | 824.0 ± 90.5 |  |
|  | 60 | 648.2 ± 25.2** |  |
|  | 80 | 482.3 ± 51.2** |  |
| Prednisolone | 20 | 440.6 ± 33** | 0.55 ± 0.1** |
|  | 40 | 488.2 ± 96.5* |  |
|  | 60 | 711.3 ± 69.3** |  |
|  | 80 | 717.6 ± 31.1** |  |

**P < 0.01;
*P < 0.05 vs. control

EXAMPLE 2

The effectiveness of naproxcinod, isosorbide dinitrate (ISD) alone and in combination with ibuprofen, molsidomine and prednisolone were evaluated using a test of functional recovery in a mouse model of muscular dystrophy (α-SG-null mice). The experiments to assess the functional recovery in α-SG-null mice were performed according to the following experimental protocol. All experiments and functional evaluations were performed by the same operator in the same laboratory.

Animal Treatment and Protocols

α-SG-null mice were housed in a pathogen-free facility, treated in accordance with the European Community Guidelines and with the approval of the Institutional Ethical Committee. Mice were given the following treatments: 3 mg/kg of molsidomine, 30 mg/kg of naproxcinod, 30 mg/kg of ISD alone and in combination with 50 mg/kg of ibuprofen, or 2 mg/kg of prednisolone incorporated in the diet. Control groups received the same diet without any drugs. Standard diet and diets containing the drugs were prepared based on the daily food intake of 3 g. Mice were treated starting at 1 month of age.

In Vivo Functional Test: Resistance to Fatigue (Exhaustion) by Treadmill

Analyses were carried out using a six-lane motorized treadmill (Exeter 3/6 treadmill, Columbus Instruments, OH, USA) supplied with shocker plates. The initial trials were performed at low intensity and for a short duration of time to get mice accustomed to the exercise; the treadmill was then run without inclination at 5 m/min for 5 min, after which the speed was increased 1 m/min every 3 min until a speed of 10 m/min was reached. The test was stopped when the mouse remained on the shocker for 20 sec without attempting to reengage the treadmill.

The data summarized in Table 1 show the effects of the tested compounds on muscle function (extent of benefit (%)). The extent of benefit (%) is expressed as the percent of the improvement of treated mice (diet containing the drug) compared to untreated mice (standard diet) on the exhaustion time. Naproxcinod showed a superior amelioration of the muscle function compared to both molsidomine and ISD alone, a co-administration of ISD and ibuprofen, or prednisolone,

TABLE 1

| Compound | Extent of the benefit (%) | Months of treatment |
|---|---|---|
| naproxcinod | 150 | 4 |
| molsidomine | 63 | 8 |
| ISD | 10 | 4 |
| ISD | 21 | 8 |
| ISD + ibuprofen | 40 | 4 |
| ISD + ibuprofen | 63 | 8 |
| prednisolone | 117 | 6 |
| prednisolone | 100 | 12 |

We claim:

1. A method of treating muscular dystrophies comprising administering to a subject a nitric oxide releasing compound of formula (Ia)

M—X—Y—ONO$_2$   (Ia)

or enantiomers or diastereoisomers thereof, wherein in the general formula (Ia), M, X and Y have the following meanings:

M is a residue

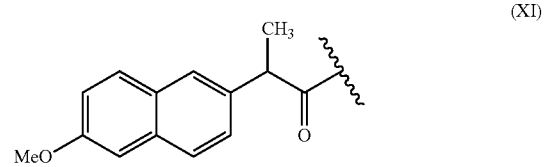 [SMILES: *C(=O)C(C)c1ccc2cc(OC)ccc2c1]

(XI)

X is —O—, —S— or —NR$^1$—, wherein R$^1$ is H or linear or branched C$_1$-C$_6$ alkyl;

Y is a bivalent radical having the following meanings:
   straight or branched C$_1$-C$_{20}$ alkylene being optionally substituted with one or more of the substituents selected from the group consisting of: halogen atoms, hydroxy, —ONO$_2$ and T, wherein T is —OC(O)(C$_1$-C$_{10}$ alkyl)-ONO$_2$ or —O(C$_1$-C$_{10}$ alkyl)-ONO$_2$; or
   —C$_5$-C$_7$ cycloalkylene group optionally substituted with linear or branched C$_1$-C$_{10}$ alkyl group.

2. The method of claim 1, wherein X is —O— and Y is a straight C$_4$ alkylene chain.

3. The method of claim 1, wherein the muscular dystrophy is Duchenne Muscular Dystrophy.

4. The method of claim 2, wherein the muscular dystrophy is Duchenne Muscular Dystrophy.

* * * * *